United States Patent
Araki et al.

(10) Patent No.: US 7,756,574 B2
(45) Date of Patent: Jul. 13, 2010

(54) BIOLOGICAL SIGNAL UTILIZING APPLIANCE AND METHOD FOR CONTROLLING THE SAME

(75) Inventors: Shoichi Araki, Osaka (JP); Koji Morikawa, Kyoto (JP); Shinobu Adachi, Neyagawa (JP)

(73) Assignee: Panasonic Corporation, Osaka (JP)

( * ) Notice: Subject to any disclaimer, the term of this patent is extended or adjusted under 35 U.S.C. 154(b) by 1198 days.

(21) Appl. No.: 11/326,923

(22) Filed: Jan. 6, 2006

(65) Prior Publication Data

US 2006/0114222 A1 Jun. 1, 2006

Related U.S. Application Data

(63) Continuation of application No. PCT/JP2005/011854, filed on Jun. 28, 2005.

(30) Foreign Application Priority Data

Jul. 2, 2004 (JP) .............................. 2004-197312

(51) Int. Cl.
*A61B 5/00* (2006.01)
(52) U.S. Cl. ..................................................... 600/544
(58) Field of Classification Search ........................ None
See application file for complete search history.

(56) References Cited

U.S. PATENT DOCUMENTS

2005/0070810 A1* 3/2005 Kennedy .................... 600/544

FOREIGN PATENT DOCUMENTS

| JP | 2000-235588 | 8/2000 |
| JP | 2002-281186 | 9/2002 |
| WO | WO-2005/001677 A1 | 1/2005 |

OTHER PUBLICATIONS

Shalk et al, "EEG-based Communication: Presence of an Error Potential," Clinical Neurophysiology, vol. 111, issue 12, Dec. 2000, pp. 2138-2144.*

* cited by examiner

*Primary Examiner*—Robert L Nasser
(74) *Attorney, Agent, or Firm*—Harness, Dickey & Pierce, P.L.C.

(57) ABSTRACT

In a biological signal utilizing appliance, an appliance control section controls the appliance in accordance with user's manipulation. At that time, an operation content is presented to a user through an operation presentation section. A biological signal detection section measures user's biological signal and detects from the biological signal the presence or absence of an event-related potential at the time point when time obtained by adding a predetermined shift time of approximately 150 ms to 600 ms elapses after a timing, as a starting point, when the operation content is presented. Upon detection of the event-related potential, a manipulation cancellation section instructs the appliance control section to cancel the presented operation content.

9 Claims, 16 Drawing Sheets

FIG.13

|  | Number of targets | Correct judgment | Identification rate(%) |
|---|---|---|---|
| Subject A | 23 | 18 | 78 |
| Subject B | 17 | 14 | 82 |
| Subject C | 18 | 16 | 89 |
| Subject D | 17 | 13 | 76 |
| Total | 75 | 61 | 81 |

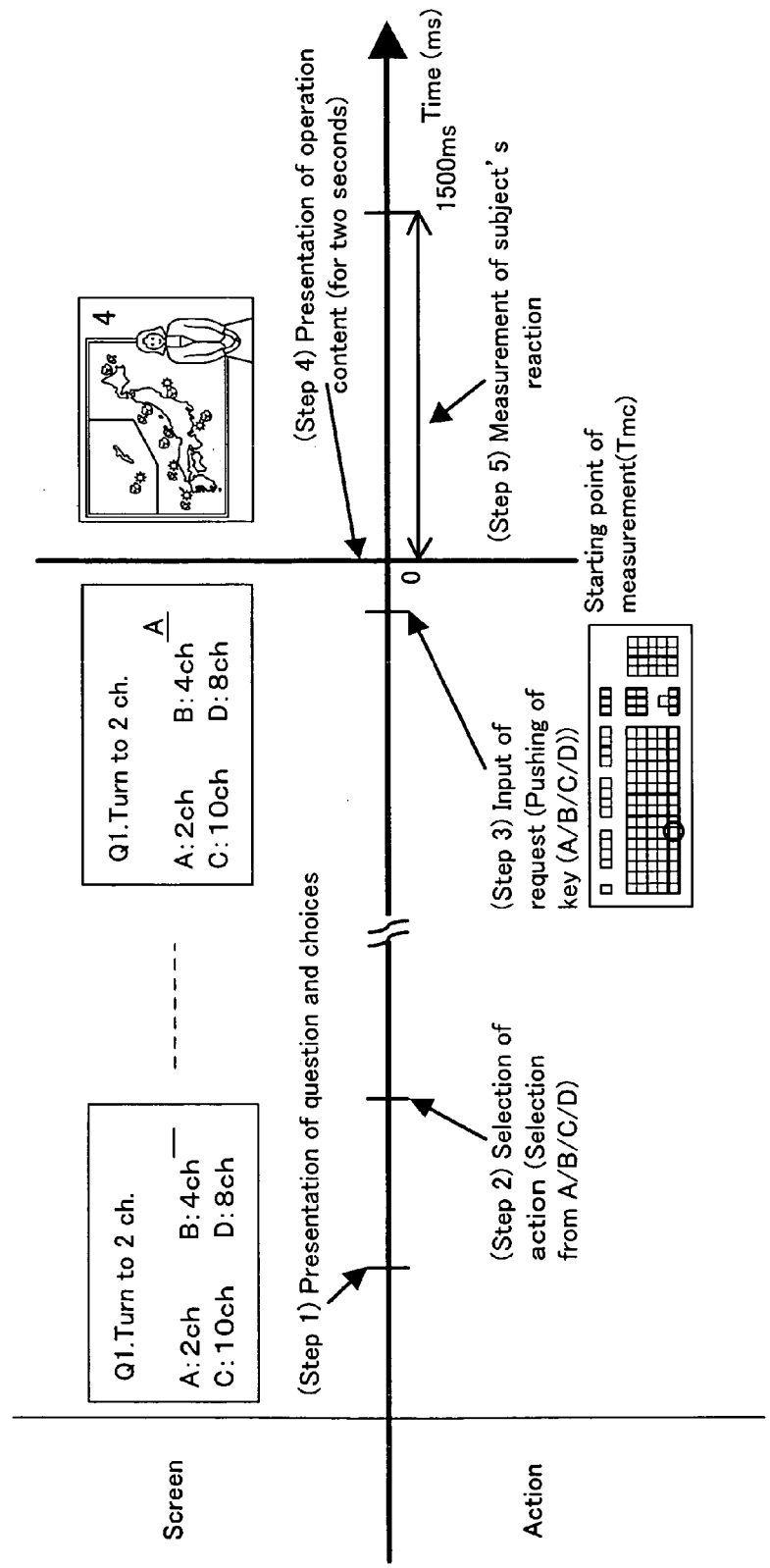

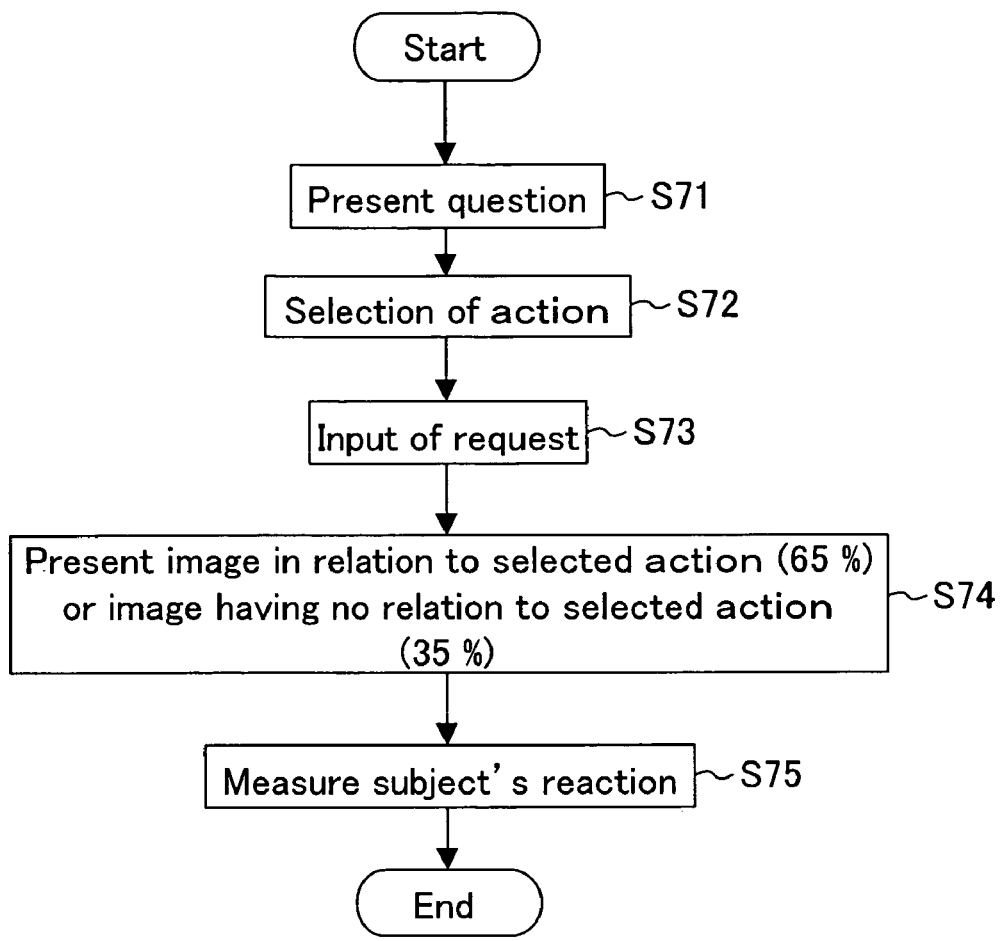

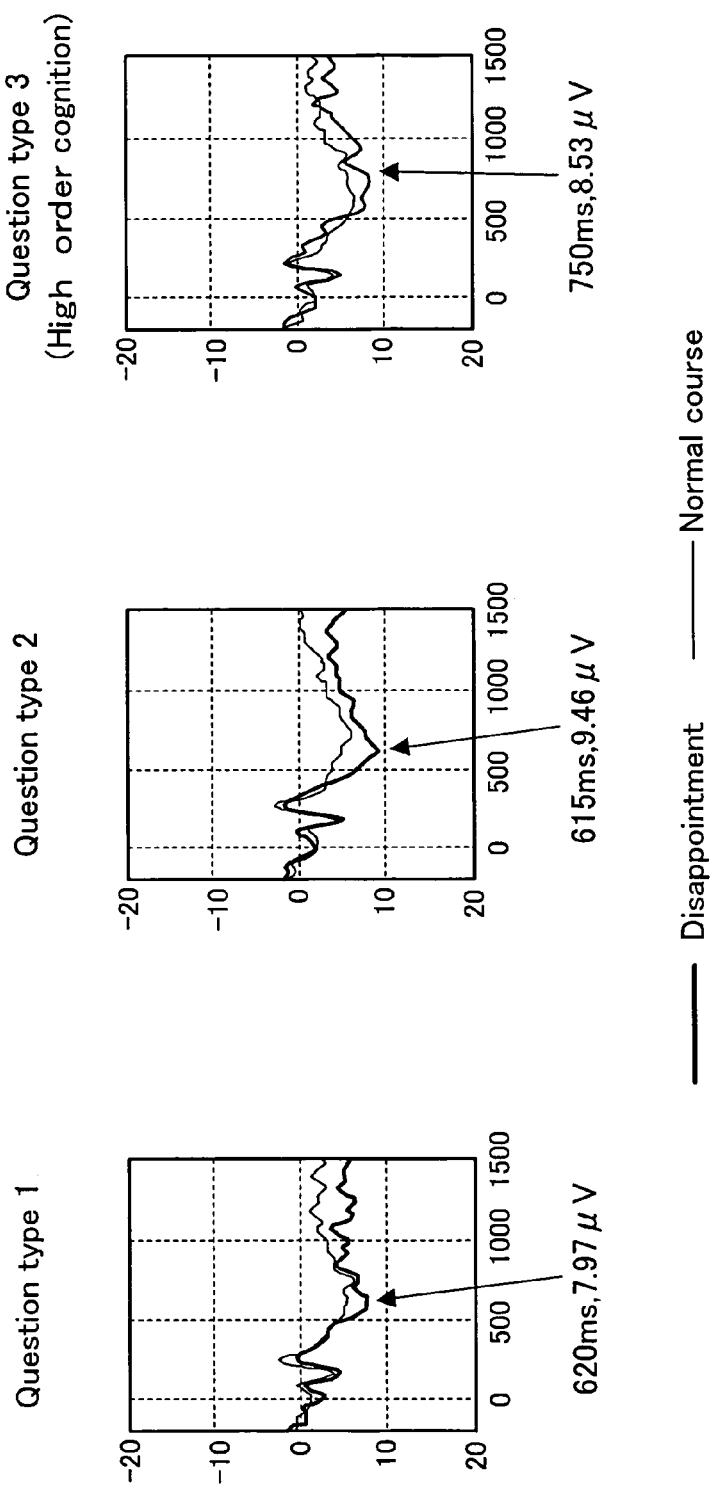

BIOLOGICAL SIGNAL UTILIZING APPLIANCE AND METHOD FOR CONTROLLING THE SAME

CROSS REFERENCE TO RELATED APPLICATIONS

This is a continuation of Application PCT/JP2005/11854, filed on Jun. 28, 2005. This Non-provisional application claims priority under 35 U.S.C. §119(a) on Patent Application No. 2004-197312 filed in Japan on Jul. 2, 2004, the entire contents of which are hereby incorporated by reference.

BACKGROUND ART

The present invention relates to control for an appliance that a user manipulates and particularly relates to a technology for appliance control utilizing user's biological signal such as an electroencephalogram (EEG).

Of conventional techniques for appliance control utilizing a biological signal such as an electroencephalogram, there is a technique utilizing a beta wave (12 to 25 Hz), which is a frequency component of an electroencephalogram capable of being generated intentionally and voluntarily. In this technique, software switches (menu items) to which intention to be conveyed (for example, nurse call, drink, and the like), which are expressed in the form of letter or figure, are allotted are displayed in matrix on a display or the like for presentation to a user and each software switch is highlighted sequentially at predetermined time intervals. When a menu item that a user desires is highlighted, the user selects the menu item by generating the beta wave. This enables a user incapable of conveying his/her intention through language and body gesture to convey his/her intention to the others.

On the other hand, in cognitive psychology and clinical medical science, study employing physiological indexes such as an electroencephalogram and the like has progressed. For example, diagnoses of dementia, melancholia, schizophrenia, hyperactive disorder, and the like and effectiveness judgments of various medicine and rehabilitation are carried out using electroencephalographs.

However, in the aforementioned conventional techniques, the timing that the beta wave should be generated may shift or the beta wave may be generated according to a physical state, unintentional motion, or the like at a timing different from user's intention. In these cases, the user cannot convey his/her intention correctly and cannot manipulate the appliance as desired. Further, it is already known that rather patience is required for acquiring the technique of generating the beta wave. Thus, the beta wave is not necessarily appropriate for controlling an appliance.

SUMMARY OF THE INVENTION

The present invention has been made in view of the above problems and has its object of enhancing convenience of an appliance by automatically modifying appliance's operation through detection of user's intention or state of mind while utilizing a biological signal.

In the present invention: a biological signal of a user manipulating an appliance is measured; when the appliance operates in accordance with the user's manipulation, the presence or absence of a disappointment signal is detected from the measured biological signal in a predetermined time range after presentation of an operation content of the appliance to the user, particularly, in a time range including a time point, as a center, when time obtained by adding a predetermined shift time around 150 ms to 600 ms elapses after the presentation; and then, the appliance is instructed to modify the operation when the disappointment signal is detected.

According to the present invention, when a user sees a presented operation content of the appliance's operation in accordance with the user's manipulation and the user feels "disappointment" like a mismatch feeling that the presented content is different from user's expectation, the disappointment is detected from the biological signal, so that the appliance's operation is modified spontaneously. This eliminates the need of re-manipulation by the user feeling disappointment, enhancing convenience of the appliance remarkably.

For modifying the operation upon detection of the disappointment signal, the operation of which content is presented to the user may be canceled or the currently executed function may be changed to another function in a case of the appliance having a plurality of functions. Alternatively, in the case where a user manipulates an appliance system including a plurality of appliances, another appliance may be operated in exchange for the currently operating appliance.

In the present description, the disappointment signal means a characteristic signal detected from a biological signal of a user when appliance's operation as a user expects before manipulation is different from actual operation result of the appliance after the manipulation. Specifically, the disappointment signal can be detected from an event-related potential of an electroencephalogram, for example.

BRIEF DESCRIPTION OF THE DRAWINGS

FIG. 13 is a table showing results of detection of the disappointment signal.

FIG. 14 is an illustration showing a scheme in sequence of an additional experiment that the present inventors carried out.

FIG. 15 is a flowchart showing a sequence for one trial of the experiment in FIG. 14.

FIG. 16 includes graphs showing experiment data relating to Question types 1 to 3.

DESCRIPTION OF THE PREFERRED EMBODIMENTS

Figure 1:
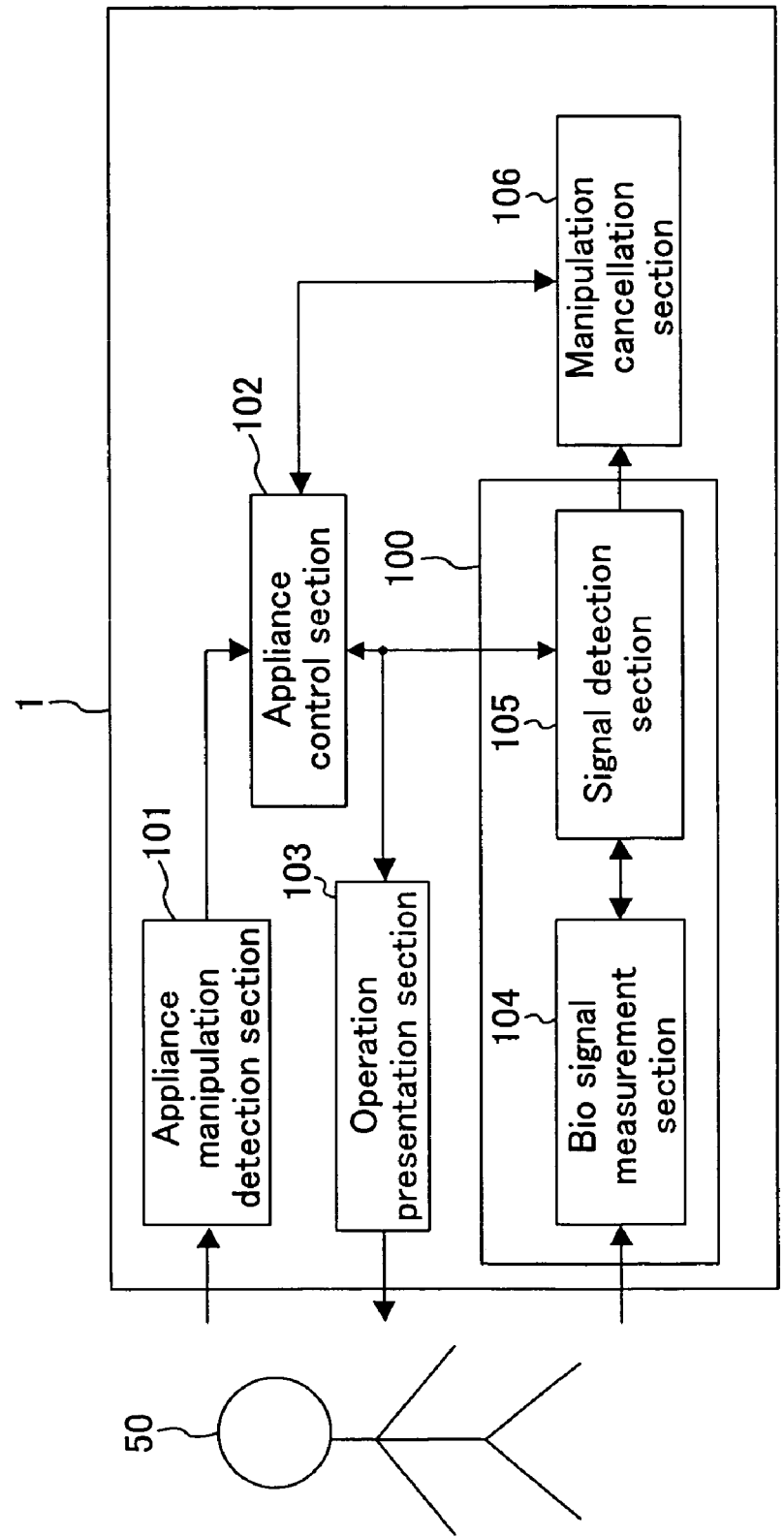
FIG. 1 is a block diagram showing a constitution of a biological signal utilizing appliance according to Embodiment 1.

In the first aspect of the present invention provides an appliance that operates utilizing a biological signal, including: an appliance manipulation detection section that detects appliance's manipulation by a user; an appliance control section that controls the appliance in accordance with the manipulation; an operation presentation section that presents to the user an operation content of the appliance as a result of the control; a biological signal measurement section that measures an event-related potential in an electroencephalogram of the user; and a signal detection section that detects the presence or absence of the event-related potential at a time point when time obtained by adding a predetermined shift time of approximately 150 ms to 600 ms elapses after a timing, as a starting point, when the operation content is presented.

Specifically, the biological signal utilizing appliance of the first aspect further includes: an operation modification section that instructs the appliance control section to cancel the manipulation of the appliance or to change a function that the appliance currently executes to another function. More specifically, the function is performance selected from a group consisting of display, selection, recording, playback, edition, distribution, and deletion of a content composed of at least one of a still image, a moving picture, a video, and audio.

While, the second aspect of the present invention provides an appliance system including the biological signal utilizing appliance of the first aspect including: an appliance change section that instructs the appliance control section to allow another appliance to operate in exchange for an appliance operating in accordance with the manipulation when the event-related potential is detected. More specifically, the appliance has at least one of functions of display, selection, recording, playback, edition, distribution, and deletion of a content composed of at least one of a still image, a moving picture, a video, and audio.

Further, the third aspect of the present invention provides a biological signal processor including: a bio signal measurement section that measures an event-related potential in an electroencephalogram of a user; and a signal detection section that detects the presence or absence of the event-related potential at a time point when time obtained by adding a predetermined shift time of approximately 150 ms to 600 ms elapses after a timing of a reaction of the appliance to the appliance's manipulation by the user as a starting point.

Moreover, the fourth aspect of the present invention provides a method for controlling an appliance that utilizes a biological signal including the steps of: detecting appliance's manipulation by a user; controlling the appliance in accordance with the manipulation; presenting to the user an operation content of the appliance as a result of the control; measuring an event-related potential in an electroencephalogram of the user; and detecting the presence or absence of the event-related potential at a time point when time obtained by adding a predetermined shift time of approximately 150 ms to 600 ms elapses after a timing, as a starting point, when the operation content is presented.

(Experiment for Obtaining "Disappointment Signal," Mismatch Feeling Signal)

An experiment for obtaining the disappointment signal, which the present inventors carried out, will be described below.

Figure 9:
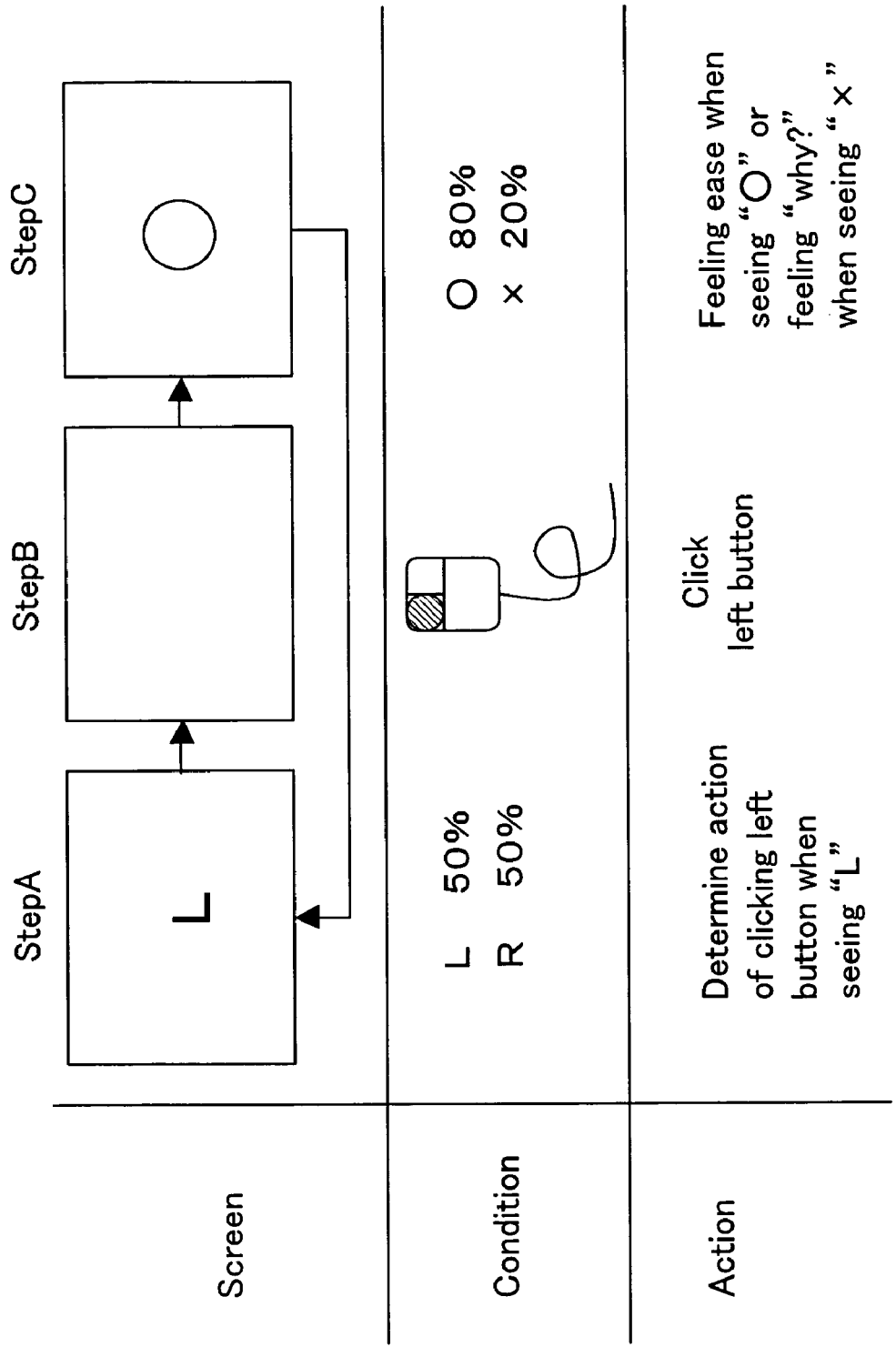
FIG. 9 is an illustration showing a scheme in sequence of an experiment that the present inventors carried out.

FIG. 9 is an illustration showing a scheme in sequence of the experiment. This experiment is composed of sequential steps of: providing an instruction to a subject (Step A); in response to the instruction, allowing the subject to think about necessary action and to manipulate an appliance (Step B); and presenting appliance's operation to the subject as a result of the subject's manipulation (Step C).

First, an experiment executer explains to a subject "When a letter 'L' or 'R' is indicated in a screen, please click the left button of a mouse for the letter 'L' or click the right button thereof for the letter 'R'." Then, "L" or "R" is selected at random at a probability of 50% and is displayed on the screen (Step A). The subject looks at the displayed letter and clicks the right or left button in accordance with the directed rule (Step B). In response to the subject's manipulation, whether or not the correct button was clicked is displayed as "○" symbol (indicating a correct answer) or "x" symbol (indicating an incorrect answer) on the screen (Step C).

Wherein, even when a correct button is clicked (clicking might be almost 100% correctly done), "x" is displayed at a probability of 20% in this experiment. When "x" is displayed, the subject, who is expecting that "○" will be displayed because of correct clicking, might think "Why?" Namely, the subject falls in a "disappointment" state in which the appliance operates differently from his/her expectation. This experiment is aimed at confirming whether or not this "disappointment" state can be detected from an event-related potential in an electroencephalogram.

Figure 10:
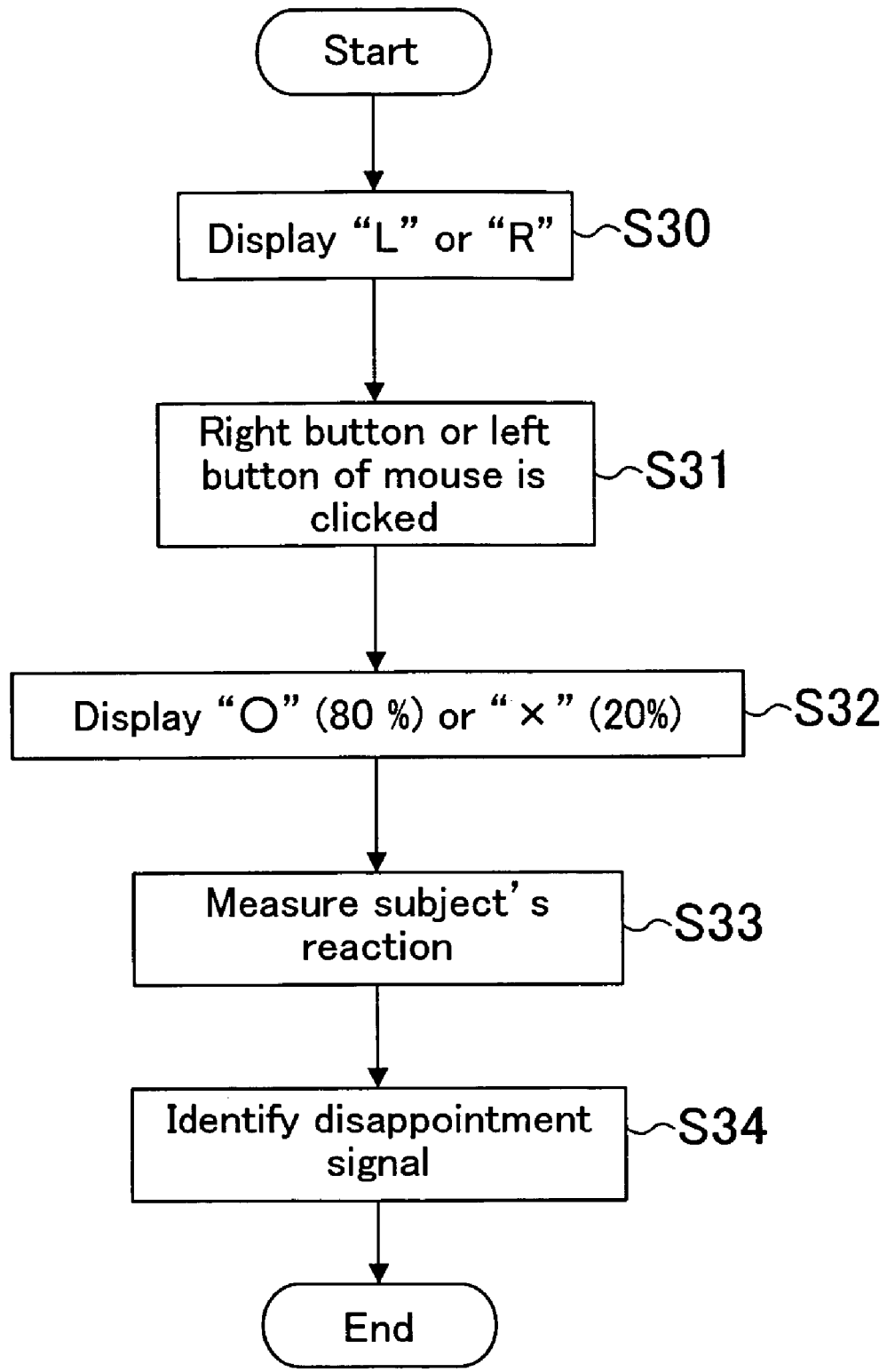
FIG. 10 is a flowchart showing a sequence for one trial of the experiment in FIG. 9.

FIG. 10 is a flowchart showing a sequence for one trial. First, the letter "L" or "R" is selected by an experiment system at a probability of 50% and is displayed on the screen (S30), the subject looks at the screen, selects which button should be clicked, and manipulates the mouse (S31). In response to the subject's manipulation, "○" or "x" is displayed on the basis of whether or not the mouse is manipulated correctly. Wherein, "x" is displayed at a probability of 20% even when "○" should be displayed (S32). The event-related potential in the electroencephalogram of the subject is measured from the timing when "○" or "x" is displayed as a starting point (S33), and the thus measured event-related potential is processed to identify the disappointment signal (S34).

In the experiment, to a plurality of subjects, a trial in which "○" is displayed every time was carried out 30 times first as practice period, and then, the trial through the sequence shown in FIG. 10 was carried out 100 times.

Figure 11:
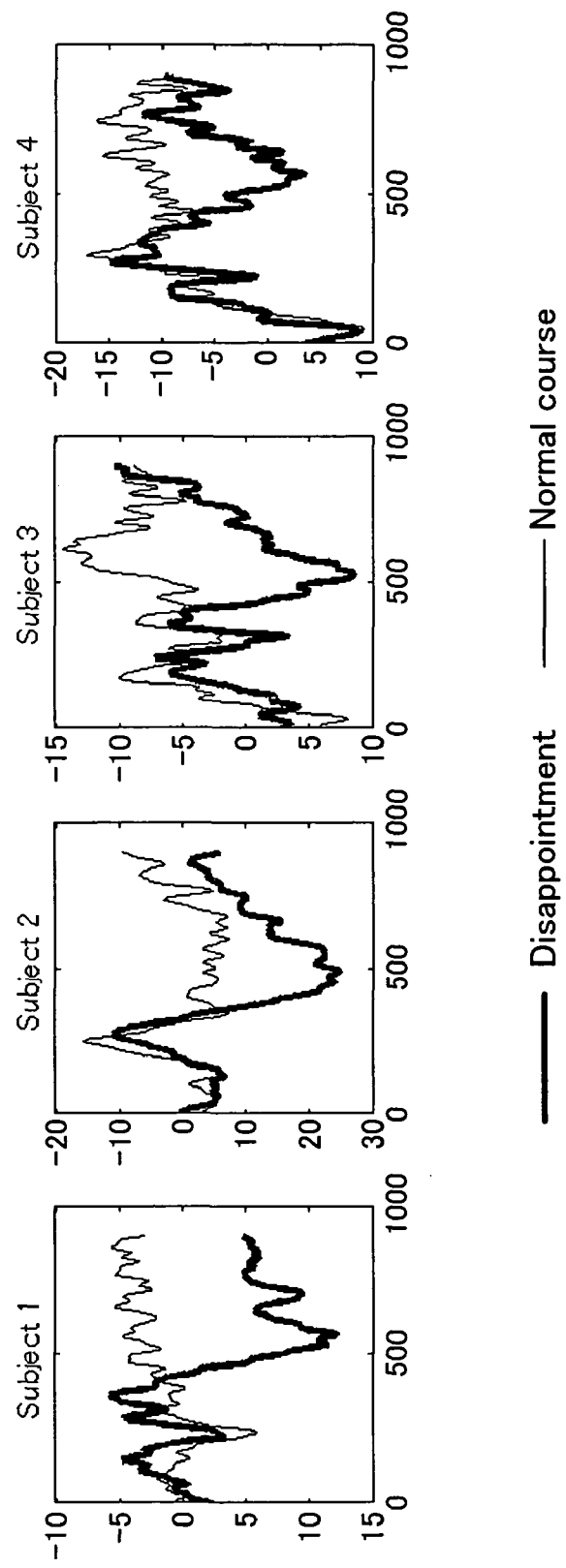
FIG. 11 includes graphs indicating experimental data of four subjects.

FIG. 11 includes graphs showing experimental data of four subjects (Subject 1 to 4) out of the experimental results. Each graph in FIG. 11 was obtained by averaging potential waveforms measured by an electroencephalograph, wherein each axis of abscissas indicates elapsed time from stimulation presentation (the time when "○" or "x" is displayed, unit: ms) and each axis of ordinates indicates potential (unit: μV). Each bold line indicates disappointment, that is, a waveform obtained when "x" was indicated in response to correct clicking and each fine line indicates a normal course, that is, a waveform obtained when "○" was indicated in response to correct clicking. Wherein, four electrodes 1) Pz, 2) and 3) A1 and A2, and 4) body earth (Z) were attached to a median vertex, respective ears, and a root of nose, respectively in accordance with the international 10-20 system. The sampling frequency was set to be 1000 Hz.

It is understood from each graph in FIG. 11 that at disappointment, an event-related potential having a characteristic different from that of a potential at the normal course appeared around approximately 600 ms after the stimulation presentation. Namely, it is expected that measurement of the event-related potential leads to detection of user's disappointment.

Wherein, in the event-related potential measured in this experiment, reaction time in response to the stimulation provision was later than P300, which is known conventionally as time when a reaction appears. The reason therefor might be as follows.

The experiments conventionally carried out in relation to event-related potentials were experiments through measurement of passive reactions of judgment on difference in sound or in image. In contrast, in the experiment that the present inventors carried out, an action was selected with a certain expectation and whether or not operation was performed as expected was judged. The feature that the step of selecting an action by a user is included is the significant difference from the conventional ones. The judgment as to whether or not the operation is performed as a subject expects is cognitive judgment compared with the mere judgment of difference in sound or in image. For this reason, the reaction time after the stimulation provision might be slightly later than that in the measurements in the conventional experiments, resulting in a peak around 600 ms after the stimulation provision.

It is noted that though the timing when a peak appears is different from subject to subject and different from trial to trial, as can be understood from FIG. 11, the presence or absence of the disappointment signal can be detected by checking the range of the event-related potential around 600 ms after the stimulation provision.

As clarified through the experiment, the event-related potential measured by the electroencephalograph offers apparent difference between the case where the appliance operates as a user expects and the case where it operates differently from user's expectation. Accordingly, the event-related potential can be used as the "disappointment signal" in the interface of an appliance.

(Detection of Disappointment Signal)

A specific example of a disappointment signal detection method will be described with reference to the flowchart of FIG. 12. In this method, a standard waveform (a target template) to which a signal at disappointment is averaged and another standard waveform (referred to as a control template) to which a signal in a non-disappointed normal state is averaged are generated in advance and these templates are utilized for detection of the disappointment signal.

Figure 12:
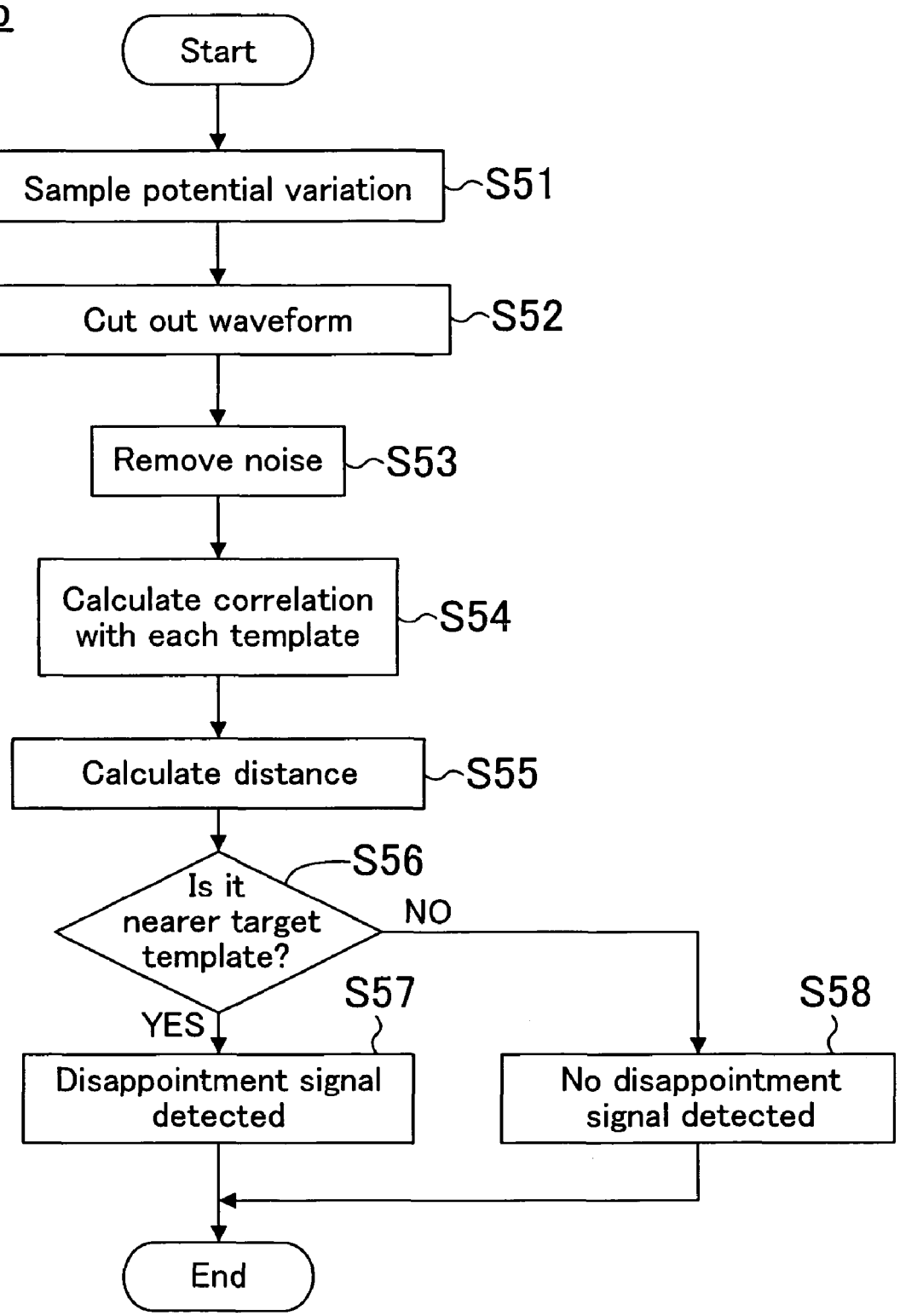
FIG. 12 is a flowchart showing an example of a specific method for detecting a disappointment signal.

As shown in FIG. 12, first, potential variation in an electroencephalogram is sampled (S51) from a timing, as a starting point, when a response content is output (at response presentation). The sampling frequency may be 200 Hz, 500 Hz, 1000 Hz, or the like, for example. Then, a waveform in a range relating to detection of the disappointment signal is cut out from the thus obtained potential variation in the electroencephalogram (S52). From the results of the above described experiment, it is known that the disappointment signal is detected at a part around 600 ms after stimulation provision. Further, in a comparatively earlier range after response presentation, a waveform appearing in response to aural stimulation or visual stimulation is considered to have no relationship with human's expectation, and therefore, the part corresponding thereto is preferable to remove. As such, the range between 200 ms and 800 ms after the response presentation is cut out.

Of course, the cut out range is not limited thereto and may be set in a range between 500 ms and 700 ms, between 300 ms and 900 ms, or the like. Alternatively, a range within approximately 1 second after the response presentation may be cut out with no early limit set.

Next, noise is removed from the cut out waveform (S53). Herein, high-frequency components mixed with the signal is cut, the signal is allowed to pass through a low-pass filter of, for example, 40 Hz, a waveform with an amplitude over 40 μV is removed from an object to be identified for reducing influence of electrooculogram by a blink, or the like.

Subsequently, each correlation between the signal from which noise is removed and the signal templates of the target template and the control template is calculated (S54). This correlation calculation calculates how the signal waveform correlates with each template.

Each distance between the signal waveform and the templates is calculated (S55). For example, Mahalanobis distance is employed for the distance calculation. This Mahalanobis distance indicates a distance from a gravity of a group taking account of variance and covariance of data. With the use of Maharanobis distance, judgment is performed as to which template the signal waveform is nearer (S56). It is known that the judgment utilizing Maharanobis distance exhibits higher recognition ability than judgment according to mere correlation magnitude.

When it is judged that the signal waveform is nearer the target template (YES in S56), it is recognized that the disappointment signal is detected, namely, that the user might be disappointed (S57). On the other hand, when it is judged that the signal waveform is near the control template (S58), it is recognized that the disappointment signal is not detected, namely, that the user thinks that the response as expected is obtained.

Employment of the method using such templates enables detection of the disappointment signal to some extent in an electroencephalogram, of which waveform includes severe variation, and accordingly, of which recognition from a single waveform is considered to be difficult.

FIG. 13 is a table showing results of disappointment signal detection in accordance with the flow of FIG. 12 using the aforementioned experiment data. FIG. 13 indicates the number of targets of each subject (number of data of disappointment) and the number of times of correct judgment. It is understood from FIG. 13 that the state of disappointment can be recognized at an accuracy of approximately 80% even from a single waveform.

It is noted that the signal templates of the target template and the control template are used herein but only the target signal template may be used. For example, Maharanobis distance from the target signal template is calculated and is compared with a predetermined value to judge whether or not the disappointment signal is detected.

It is also noted that another method may be employed rather than the use of a template or in combination with the use of a template. For example, a local maximum or a local minimum may be used, or it is possible that a maximum positive component in a waveform is detected and the amplitude thereof is compared in magnitude with a threshold value. Alternatively, an adaptive correlating filter may be used. It might be possible to provide various additional improvements in the waveform recognition method, and the recognition accuracy might be increased by, for example, combination of a pattern recognition method and a pretreatment method for an electroencephalogram signal.

(Experiment for Obtaining Disappointment Signal Based on High Order Cognition)

The present inventors carried out an additional experiment for obtaining the disappointment signal. This experiment is aimed at confirming that a similar event-related potential appears in actual manipulation of an interface of an appliance such as manipulation for selecting a desired image in a digital TV set, for example, as well as in confirmation of an expected operation content through a simple symbol such as "○ or x." This experiment is also aimed at measuring user's reaction based on high order cognition, such as judgment as to whether or not it is as expected when a content that a subject expects and imagines at selection of a genre name or a program name is compared with an image that cannot be known to the subject prior to actual presentation thereof, as well as that based on the confirmation of expected operation through simple symbol such as a channel number. This experiment will be described below.

FIG. 14 is an illustration showing a scheme in sequence of the additional experiment. This experiment is composed of a sequential steps of: presenting a question and choices to a subject through a screen (Step 1); allowing the subject to select one of the choices which the subject judges appropriate (Step 2); allowing the subject to input a request to an appliance through a keyboard or the like as use's own request (Step 3); presenting an image on the screen as a request result after a predetermined time period elapses (Step 4); and measuring by an electroencephalograph user's reaction at judgment as to whether or not the content of the image in response to the request matches an intended content (Step 5).

FIG. 15 is a flowchart showing a sequence for one trial. First, a question and choices for action to be taken thereto are displayed concurrently on a screen to a subject (S71). For example, as shown in FIG. 14, "A: 2 ch., B: 4 ch., C: 10 ch., D: 8 ch." or the like are displayed together with a question, "Turn to 2 ch." Next, the subject recognizes the presented question and choices and selects an action to the question out of the choices (S72). For example, as shown in FIG. 14, the subject selects an action A for turning to 2 ch., and then, inputs the selected action to the appliance (S73). Specifically, the subject pushes any one of keys of a keyboard which correspond to the choices A to D. For example, as shown in FIG. 14, the subject pushes the key "A." After 200 ms elapses after the key input by the subject (S74), an image of which content matches the selected action or an image of which content is different from the selected action is presented on the screen at probabilities of 65% or 35%, respectively. Wherein, the image is presented for two seconds and the next question is presented after 0.5 second from termination of the image presentation. Further, the contents of images are changed from trial to trial. The event-related potential in an electroencephalogram of the subject is measured for a predetermined time period (1500 ms) from the time Tmc, as a starting point (time 0), when the image is presented (S75).

Herein, there are presented three types of questions: a question relating to a request through a symbol (Question type 1) such as the channel number like "Turn to 2 ch."; a question relating to a request for a program by genre (Question type 2) like "Set to a baseball program"; and a question relating to a content itself of a program (Question type 3) like "Set to News Z." The number of choices is four.

In Question types 1 to 3, presentation of an image of which content matches the selected action (hereinafter referred to as 'expected-image presentation') and presentation of an image of which content is different from the selected action (hereinafter referred to as 'different-image presentation') are as follows.

In Question type 1 (relating to a request through a symbol), for example, the expected-image presentation is presentation of an image of 2 ch. in response to input of the request for 2 ch. and the different-image presentation is presentation of an image of a different channel, for example, 4 ch. in response to the request for 2 ch. For example, FIG. 14 shows an example in which an image of 4 ch. is presented even through the subject inputs 2 ch. for requesting presentation of 2 ch.

In Question type 2 (relating to a request for a program by genre), for example, the expected-image presentation is presentation of an image of a baseball program in response to input of a request for genre of a baseball program and the different-image presentation is presentation of an image of a genre different from the requested genre of the baseball program, such as a news program, an animation program, a weather report program, or the like.

In Question type 3, (relating to a content itself), for example, the expected-image presentation is presentation of an image of "News X" in response to the request input of the program of "News X" and the different-image presentation is presentation of a different program such as "News Y." "News Z," or the like in response to the program request for "News X.".

Among Question types 1 to 3 as described above, there are following differences in cognitive complication. Namely, Question type 1 involves complication in recognition of difference in symbol such as 2 ch., 4 ch., and the like. Question type 2 involves complication in recognition of genre levels and a matter of recognizing an image composed of a figure, an object, or the like as a genre of a news program, an animation program, a baseball program, or the like, in addition to the symbols. In this matter, the animation program is apparently different from the others in color tone. Also, significant difference in category is identified among a weather chart, a ballpark, and a news studio in this matter, and thus, recognition might be easy to the same extent as the recognition of the symbols.

In contrast, Question type 3 involves complication in further recognition of a content from one of images belonging to the same genre. For example, for identifying a content with one of a plurality of images belonging to a single genre of a news program, it is required to consider further detailed characteristics such as an aspect of a studio, an appearing caster, superimposition of letters, and the like. Referring to baseball programs, for example, in order to identify a program content such as "ABC vs. XYZ," further detailed characteristics such as difference in ballpark, difference in uniform, and the like must be considered as well. In short, apparent difference in cognitive complication lies between Question type 2 in which identification can be made at a glance from difference between a ballpark and a weather chart and Question type 3 in which identification must be made between very similar matters such as ballparks, team uniforms, and the like. Higher oder cognition might be required in Question type 3.

Wherein, in the present experiment, the same images prepared for the present experiment are used in different question types. For example, in response to the request, "Set to a baseball program" in the experiment relating to Question type 2, the image of a weather report program indicated in FIG. 14 is presented as a different-image presentation. In this way, the cognitive complication differs according to the question types even when the same image is presented and how differently a subject reacts according to this difference was verified.

The present experiment in which the trial in sequence shown in FIG. 15 is performed 120 times was carried out twice to every subject, and data of 240 trials in total per subject was measured. Wherein, the method of attaching the electrodes followed the international 10-20 system as in the previous experiment and the sampling frequency was set to 200 Hz. Further, in experiment data analysis, a band-pass filter of 0.05 to 10 Hz was used and a waveform in the range from 200 ms to 0 ms prior to the simulation presentation was used for baseline correction. In addition, an electrooculogram was measured simultaneously in order to prevent noise caused due to a blink from mixing, and every trial in which an amplitude of electrooculogram component exceeds 100 μV was removed from the data to be analyzed.

FIG. 16 includes graphs showing the experiment data relating to Question types 1 to 3. Each graph in FIG. 16 was obtained by averaging potential waveforms obtained from three subjects, wherein each axis of abscissa indicates elapsed time from the image presentation (unit: ms) and the axis of ordinates indicates potential (unit: μV). Each bold line indicates a waveform obtained at presentation of an image having no relation to the input request (selected action) and each fine line indicate a waveform obtained at presentation of an image in relation to the input request (selected action).

In the graphs corresponding to Question types 1 and 2 in FIG. 16, when an image having no relation to the input request (selected action) is presented, an event-related potential having a characteristic different from that of the normal course appears after approximately 600 ms from the presentation, similar to the previous experiment result. As well, in the graph corresponding to Question type 3 in FIG. 16, apparent difference can be observed between the waveform obtained when an image having no relation to the input request (selected action) is presented (for example, an image of "News Z" is displayed in response to input of "News X" or the like) and the waveform obtained when an image in relation to the input request (selected action) is presented (for example, an image of "News X" is displayed in response to input of "News X"). Further, the latency of the characteristic event-related potential shifts by approximately 150 ms from 600 ms to around 750 ms. This might be because Question type 3 is different from Question types 1 and 2 in the above described cognitive complication.

The previous experiment confirmed that the judgment as to whether or not operation is performed as a subject expects is cognitive judgment compared with mere judgment of difference in sound or in image, and accordingly, the reaction time after the stimulation provision might be slightly later than the conventionally measured event-related potentials, resulting in a peak around 600 ms after the stimulation provision.

As described above, in the present experiment, even in a case of cognitively-complicated judgment of comparison between the expected content of rough genre level and the content of actually presented operation of the appliance, it was confirmed that the characteristic event-related potential appears after approximately 600 ms from the stimulation provision, as well as in the previous experiment. From this confirmation, utilization of the event-related potential at around 600 ms must be very effective in general interface manipulation, which is usually described in genre level such as operations and functions.

Moreover, it was confirmed that in a case requiring further cognitively-complicated judgment which necessitates consideration of further detailed characteristic such as a content of the program beyond the complication that the judgment of rough difference such as genre is made, the characteristic event-related potential appears with a latency shift of approximately 150 ms. Accordingly, the latency shift of the event-related potential must be taken into consideration according to the level of cognitive complication in a real situation to which a novel interface for recognizing a further complicated state is applied.

As cleared from the additional experiment, even a case requiring further cognitively-complicated judgment, apparent difference in event-related potential measured by an electroencephalograph exists between the case where an appliance operates as a user expects and the case where the appliance operates differently from user's expectation.

Embodiments of the present invention will be described next with reference to the drawings.

Embodiment 1

FIG. 1 is a block diagram showing a constitution of a biological signal utilizing appliance according to Embodiment 1 of the present invention. In FIG. 1, a biological signal processor 100 is built in the biological signal utilizing appliance (hereinafter it may be referred to as "appliance" merely) 1. Wherein, the biological signal processor 100 may be provided separately from the appliance 1.

In FIG. 1, reference numeral 101 denotes an appliance manipulation detection section that detects appliance's manipulation by a user 50, 102 denotes an appliance control section that performs control of the appliance 1 in accordance with the manipulation by the user 50 which is detected by the appliance manipulation detection section 101, and 103 denotes an operation presentation section that presents an operation content of the appliance 1 to the user 50. Further, in the biological signal processor 100, reference numeral 104 denotes a biological signal measurement section that measures a biological signal of the user 50 and 105 denotes a signal detection section that detects the presence or absence of the disappointment signal from the biological signal measured by the biological signal measurement section 104. Reference numeral 106 denotes a manipulation cancellation section as an operation modification section that cancels, upon detection of the disappointment signal, the operation according to an operation content presented through the operation presentation section 103 and instructs to the appliance control section 102 to return the appliance 1 to the state prior to the manipulation.

In the present embodiment, the appliance automatically judges whether nor not the appliance's operation in accordance with the user's manipulation matches user's expectation, and the appliance returns to the state prior to the user's manipulation when it is against the expectation. Specifically, for example, if a user would push a wrong manipulation button in error, if the user would miss-operate the appliance because of his/her misunderstanding about the function of the manipulation button, or if the user would operate the appliance groundlessly without knowing the correct manipulation, the appliance's operation would not necessarily match user's intention. In such a case, the disappointment signal is detected utilizing a biological signal and the appliance's operation not matching the user's expectation is cancelled automatically. Whereby, the user is free from annoying manipulation for correction, enhancing convenience remarkably.

Referring to manipulation of a video tape recorder, for example, if a user who wishes fast-forwarding or fast-reverse would appropriately pushes a fast-forward button or a fast-reverse button, the video tape recorder would operate as the user intends. However, if a wrong button would be pushed, the video tape recorder would fall in a state different from his/her intention and he/she thinks "Why?" and feels disappointment. Wherein, in a case applying this to the above described experiment, L and R correspond to intended operation of fast-forward and fast-reverse, respectively, the left click button and the right click button of the mouse correspond to the fast-forward button and the fast-reverse button, respectively, and "o" and "x" displayed as the results correspond to the state of the appliance as intended and the state of the appliance different from the intention, respectively.

In the present embodiment, for example, when the appliance falls in a state against user's intention because the user pushes the fast-reverse button in error though he/she tries to fast-forward a video tape in a playback state, this can be detected from the disappointment signal. Accordingly, the appliance is allowed to cancel the wrong manipulation, that is, fast-reverse and to return the state to the original playback state. As well, excessive volume turn-up or turn-down operation can be canceled through detection of the disappointment signal.

The biological signal measurement section 104 includes an electroencephalograph to measure an electroencephalogram of the user 50 as a biological signal. The user 50 fits the electroencephalograph in advance. The optimal positions of the electrodes to be set may be determined according to an experiment, or the like.

Figure 2:
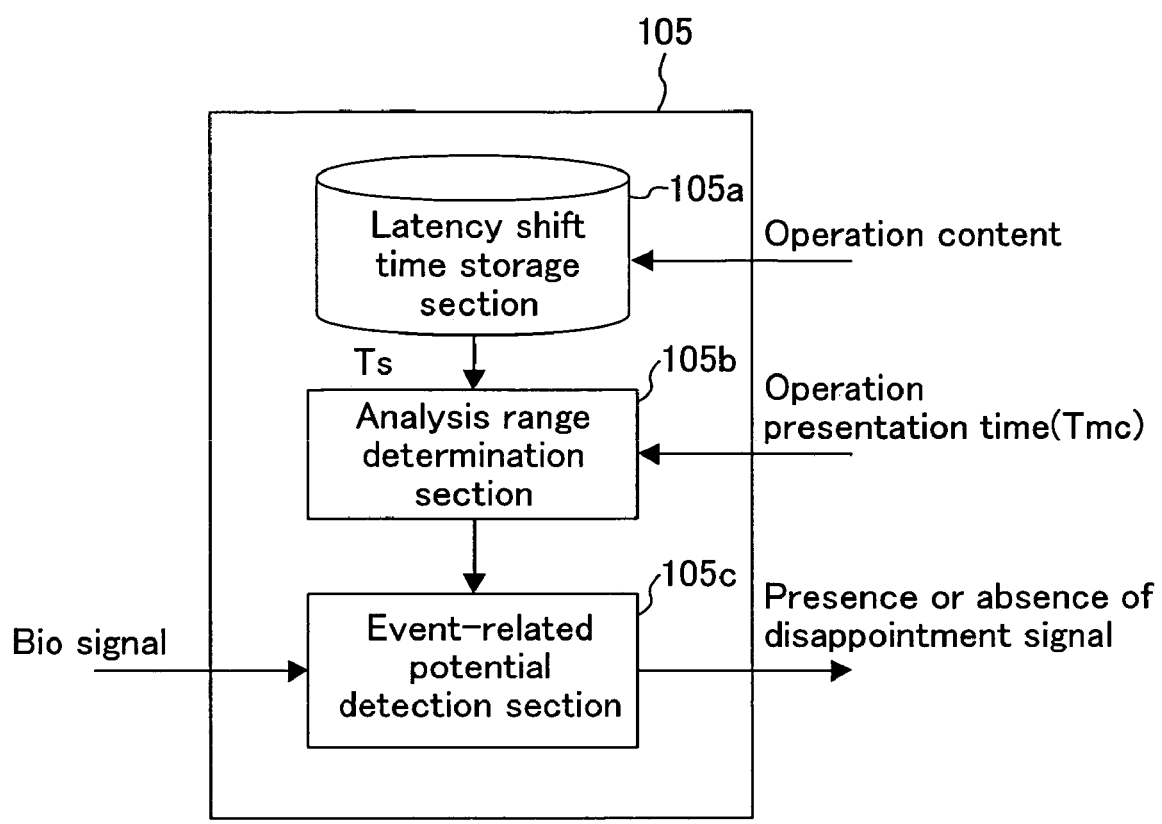
FIG. 2 is a block diagram showing an example of an internal constitution of a signal detection section in the constitution in FIG. 1.

The signal detection section 105 detects, from the electroencephalogram of the user 50 which is measured as a biological signal, the presence or absence of the disappointment signal in a predetermined time range after the operation presentation section 103 presents an operation content. FIG. 2 is a block diagram showing an example of the internal constitution of the signal detection section 105. In FIG. 2, reference numeral 105a denotes a latency shift time storage section that stores a shift time Ts in latency of the disappointment signal which varies according to cognitive complication of an operation content of the appliance, user's individuality and age, and the like, 105b denotes an analysis range determination section that determines a time range from which the presence or absence of the disappointment signal is detected while referencing the latency shift time storage section 105a, and 105c denotes an event-related potential detection section that detects the presence or absence of the disappointment signal from the electroencephalogram of the user 50 which is measured as a biological signal in the time range determined by the analysis range determination section 105b.

Figure 3:
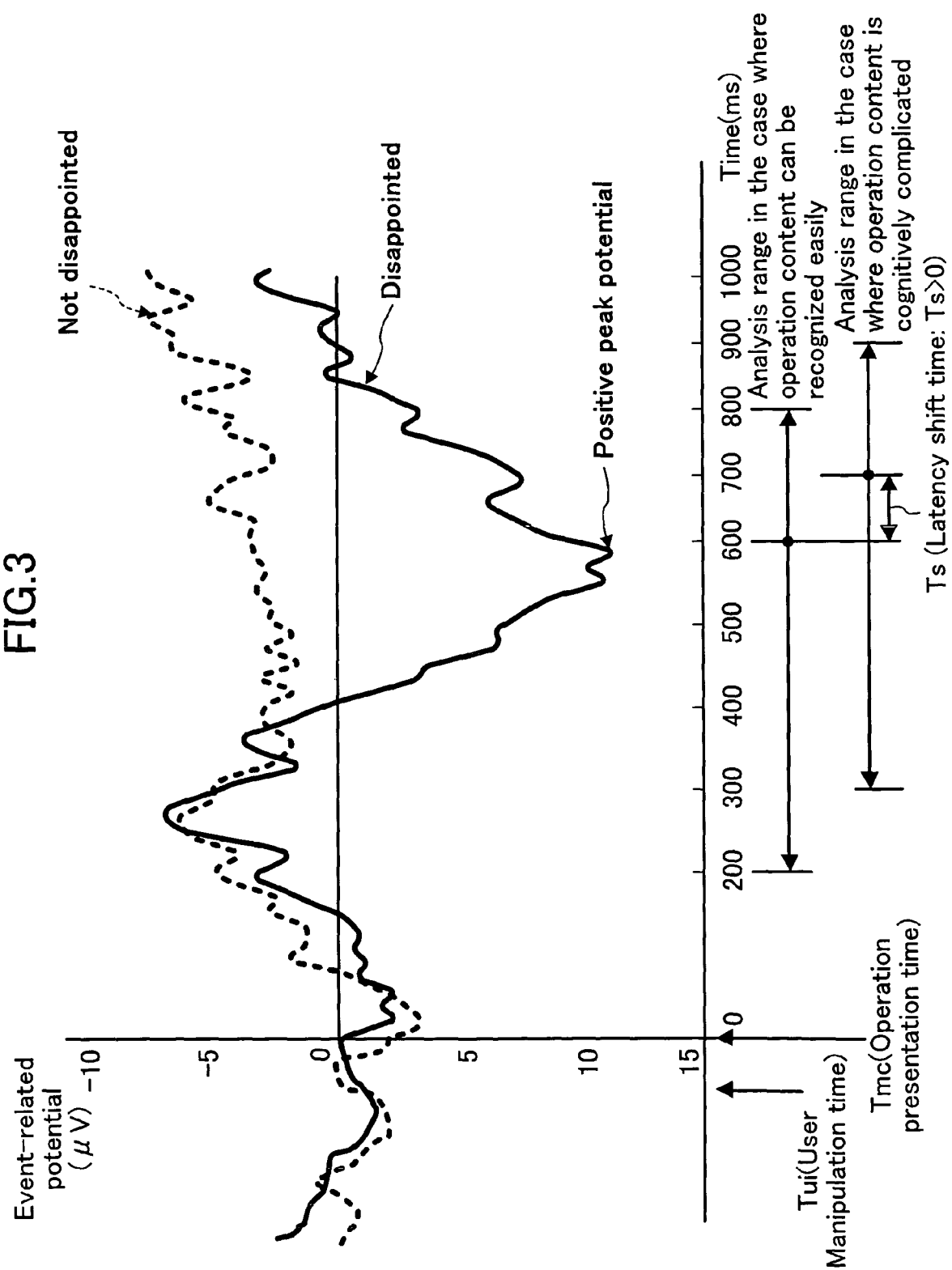
FIG. 3 shows one example of an electroencephalogram signal obtained at appliance manipulation.

FIG. 3 shows one example of the electroencephalogram obtained at appliance's manipulation by a user. As cleared from the above described experiments carried out by the present inventors, when disappointment is felt, a positive peak potential occurs at a timing when approximately 600 ms elapses after the operation presentation. In the present embodiment, a time range around (600+Ts) ms as a center is set as the disappointment signal detection range, that is, the analysis range on the time axis in which the timing when an operation content is presented to the user 50, that is, operation presentation time Tmc is set as a starting point (time 0), as shown in FIG. 3. Herein, an example is shown in which a latency shift time Ts read out from the latency shift time storage section 105a becomes a plus or minus value with respect to the latency, 600 ms, of the disappointment signal in response to easy cognition such as the presentation of "○" or "x."

Especially, as cleared from the result of the above described additional experiment, in a case requiring further cognitively complicated judgment, a time range around 750 ms as a center, which is obtained by adding a value around 150 ms as the latency shift time Ts to the latency, 600 ms, is set as the disappointment signal analysis range. Further, for example, in judgment of disappointment on the basis of cognition of a further complicated state, such as judgment as to whether or not the volume is increased as intended by pushing the volume button, judgment as to whether or not the content displayed in GUI upon menu selection matches the content as intended, and the like, the peak of the detected disappointment signal is expected to appear approximately 150 ms later than the latency, 600 ms.

Moreover, the latency shift time Ts might differ according to an operation content to be presented. Accordingly, it is preferable to store a standard latency shift time according to an operation content in advance in the latency shift time storage section 105a. The standard latency shift time may be obtained by the experiment with several subjects or the like. Alternatively, it is possible that user's manipulation history is recorded and the latency shift time is determined or modified through learning or the like from manipulation time intervals and the like. This enables dealing with user's characteristic such as difference in latency which is caused due to age, individuality, or the like.

Figure 4:
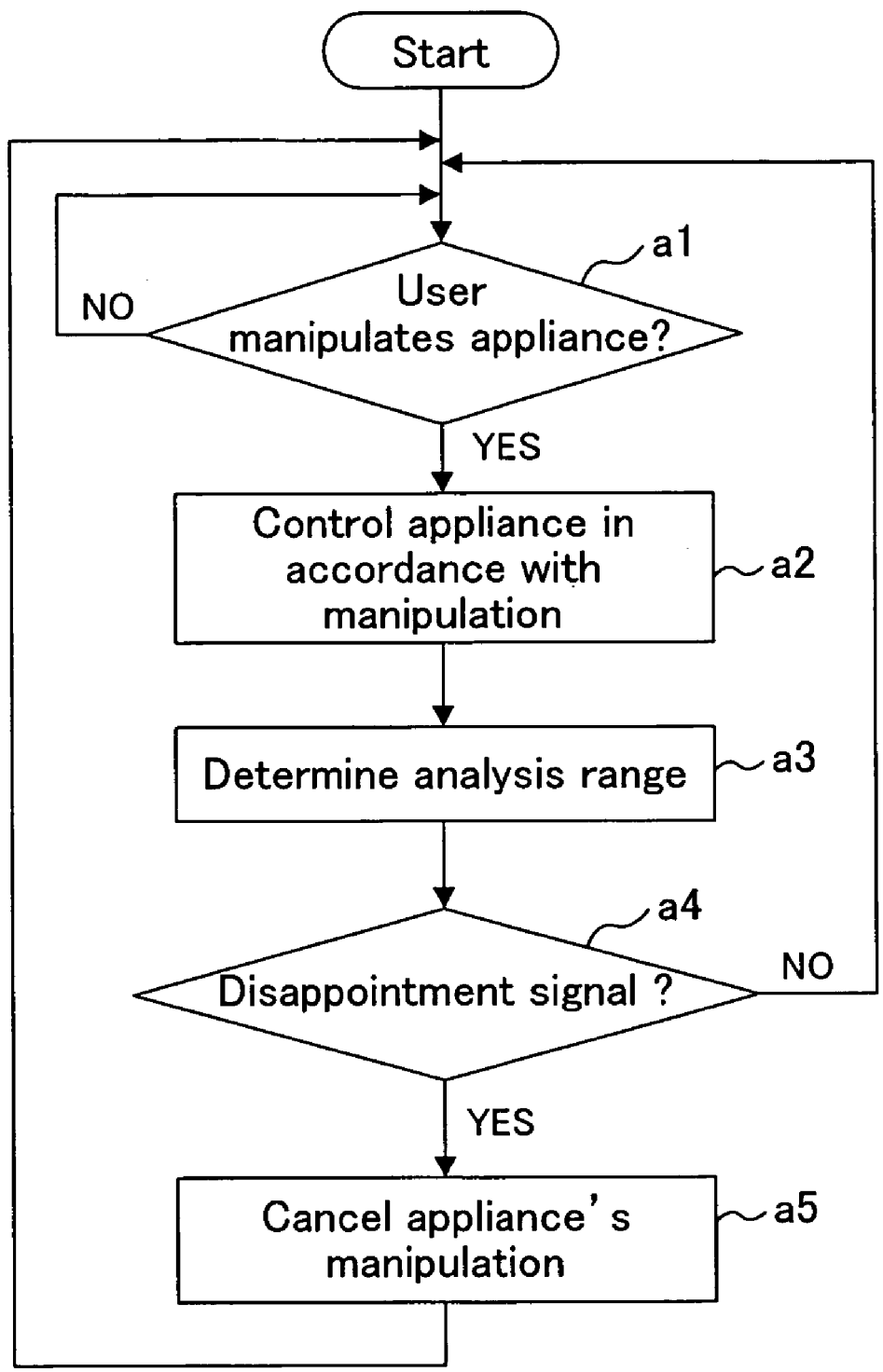
FIG. 4 is a flowchart showing operation of the constitution in FIG. 1.

Operations of the appliance 1 and the biological signal processor 101 according to the present embodiment will be described with reference to the flowchart of FIG. 4. Herein, the electroencephalogram of the user 50 is measured all the time by the biological signal detection section 104 and is recorded in time series. Wherein, the measurement of the electroencephalogram may be performed appropriately according to the timing of the appliance's manipulation by the user, appliance operation, or the like.

First, the appliance manipulation detection section 101 detects the manipulation of the appliance 1 by the user 50 (a1). When the user 50 performs some manipulation (YES in a1), the routine proceeds to a step a2. At that time, the time (user manipulation time) Tui when the user 50 performs the manipulation is recorded in the signal detection section 105 through the appliance control section 102. On the other hand, when no manipulation is input (NO in a1), the appliance 1 waits manipulation input continuously.

In the step a2, the appliance control section 102 stores the current state of the appliance prior to operation transition in response to the manipulation of the user 50. Then, the appliance control section 102 controls the appliance 1 so that the appliance operates in accordance with the manipulation by the user 50. At that time, an operation content is conveyed to the operation presentation section 103. The operation presentation section 103 presents to the user 50 the operation content received from the appliance control section 102. For example, in the case where the appliance 1 is a digital TV set, when the user 50 selects, as a manipulation input, a given menu item of GUI in an appliance setting menu, the submenu items corresponding thereto are displayed on the screen. At that time, the appliance control section 102 records in the signal detection section 105 the time (operation presentation time) Tmc when the operation content is conveyed.

Subsequently, in a step a3, the analysis range determination section 105b in the signal detection section 105 determines an analysis range, which serves as a time range from which the disappointment signal is to be detected. Herein, as shown in FIG. 3, the time range around (600 ms+Ts) ms as a center is set as the range from which the disappointment signal is to be detected, that is, the analysis range on the time axis in which the operation presentation time Tmc is set as a starting point. In the example shown in FIG. 3, a time period between 200 ms and 800 ms from the starting point is set as the analysis range. It is noted that the analysis range is not limited to that shown in FIG. 3 and may be set between 500 ms and 700 ms, between 300 ms and 900 ms, or the like. Alternatively, a range within approximately 1 second after the operation content presentation may be cut out with no lower limit set.

Next, in a step a4, the event-related potential detection section 105c in the signal detection section 105 detects, from the electroencephalogram measured by the biological signal measurement section 104, the presence or absence of the disappointment signal in the analysis range determined by the analysis range determination section 105b in the step 3a. This detection may be performed, for example, using similarity to a model waveform of the disappointment singal (utilizing a correlation coefficient, Mahalanobis distance, or the like) or through judgment as to the presence or absence of a positive peak potential with the use of a predetermined threshold value (over 10 μV, for example). When the disappointment signal is not detected (NO in a4), the routine returns to the step a1 and the control of the appliance is continued for waiting the next manipulation instruction. On the other hand, when the disappointment signal is detected (YES in a4), the routine proceeds to a step a5.

In the step a5, the manipulation cancellation section 106 instructs the appliance control section 102, upon receipt of information that the disappointment signal is detected from the signal detection section 105, to return the appliance 1 to the state prior to the manipulation. Upon receipt of the instruction, the appliance control section 102 stops the control in accordance with the user's manipulation instruction and returns the appliance 1 to the state prior to the manipulation.

As described above, in the present embodiment, the appliance automatically judges whether or not the appliance's operation in accordance with the user's manipulation matches the user's expectation, and returns the appliance to the state prior to the user's manipulation when the appliance's operation is against the expectation. Whereby, the user is free from annoying manipulation for correction, enabling smooth appliance manipulation.

It is noted that the operation cancellation described herein is one of examples and it is needless to say that various modifications are possible on the basis of the subject matter of the present embodiment that appliance's operation different from user's intention is detected and the manipulation that is the cause of the operation is cancelled.

Further, explanation with respect to the manipulation result may be displayed upon detection of the disappointment signal. For example, though a user selects a channel for trying to watch a program that the user usually watches, the program may have been changed for a special news program. In this case, the user might feel disappointment. However, if information that the program has been changed would be displayed, the user could know why the program that the user expects is not on air. If the user would know that the special program is on air today, the detection signal would not be detected. Accordingly, information that the program has been changed may not be displayed.

Moreover, as cleared from the previous experiment, it is needless to say that automatic zapping for automatically presenting a content as the user expects is enabled in such a manner that change to another cannel, presentation of a content of another genre, or presentation of another similar content is performed by the appliance control section 102 when the disappointment signal is detected in selecting a content such as a program, music, or the like and presentation of the currently presented content is maintained when the disappointment signal is not detected.

Embodiment 2

Recently, multifunction appliances, most notably home use digital appliances, are increasing, and users are required, in order to operate such a multifunction appliance, to take an action for desired manipulation after selecting in advance a function to be executed. For example, in order to play pack a content in manipulation of an appliance having functions as an HDD recorder and a DVD recorder, a user is required to select the HDD function or the DVD function first, and then, to push the playback button for playing back the content. Such a multifunction appliance has common operation buttons for playback, search, and the like in general. Accordingly, when a user who wishes to watch DVD pushes the playback button, the desired content is not played back naturally in a condition that the function mode of the appliance is set to HDD.

In Embodiment 2 of the present invention, in the case where operation in accordance with user's manipulation does not match user's intention in an appliance having plurality of different functions, the currently executed function is switched to another function automatically through detection of the disappointment signal.

Figure 5:
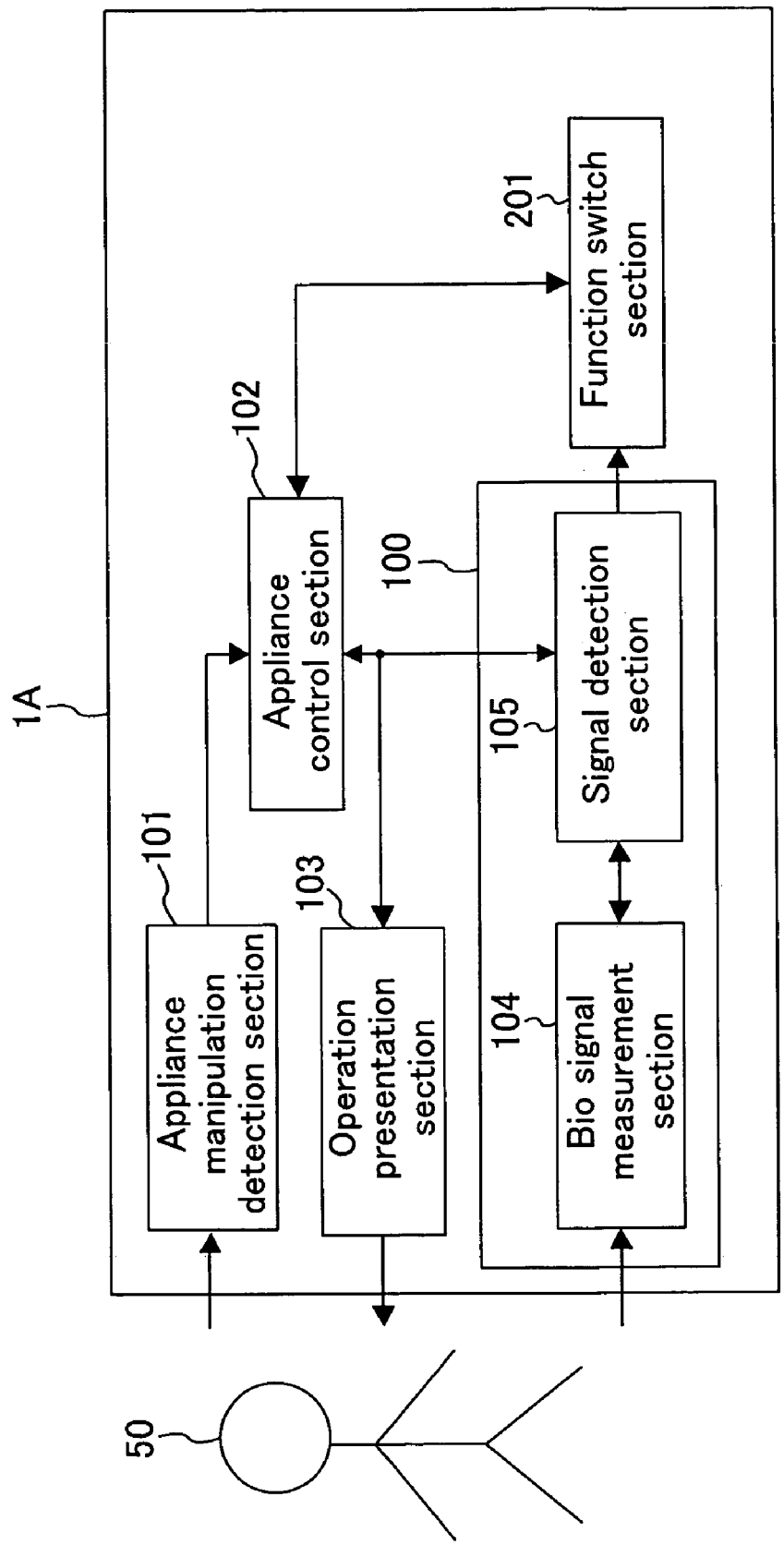
FIG. 5 is a block diagram showing a constitution of a biological signal utilizing appliance according to Embodiment 2.

FIG. 5 is a block diagram showing a constitution of a biological signal utilizing appliance according to the present embodiment. In FIG. 5, the same reference numerals are assigned to the constitutional elements common to those in FIG. 1. In the biological signal utilizing appliance 1A in FIG. 5, a function switch section 201 as an operation modification section is provided in lieu to the operation cancellation section 106. The function switch section 201 instructs the appliance control section 102 to switch the currently executed function to another function when the disappointment signal is detected by the signal detection section 105. The biological signal processor 100 is built in the appliance 1A in FIG. 5, but may be provided separately from the appliance 1A.

Figure 6:
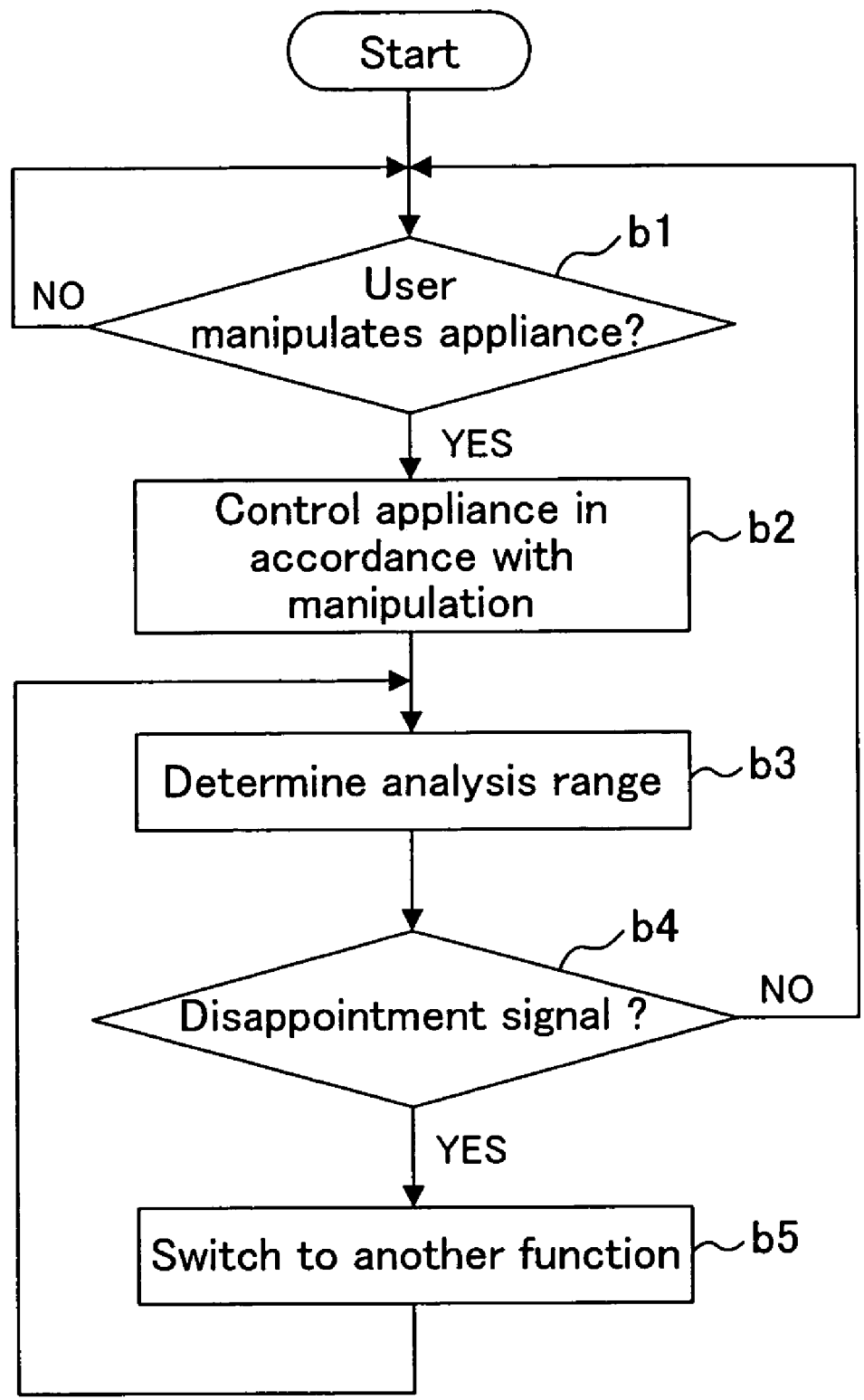
FIG. 6 is a flowchart showing operation of the constitution in FIG. 5.

Operation of the appliance 1A according to the present embodiment will be described with reference to the flowchart of FIG. 6. Wherein, steps b1 to b4 in FIG. 6 are the same as the steps a1 to a4 in Embodiment 1, and therefore, the description thereof is omitted.

When the disappointment signal is detected from the electroencephalogram of the user 50 (YES in b4), the currently executed function of the appliance 1A is changed to another function that the appliance 1A has in a step b5. In detail, the function switch section 201 instructs the appliance control section 102 to switch the currently executed function to anther function. Upon receipt of the instruction, the appliance control section 102 switches the currently executed function to another function. Then, the routine returns to the step b3 and the detection of the presence or absence of the disappointment signal is performed again.

For example, suppose that the appliance 1A is a multi function peripheral of DVD and HDD and a HDD content is played back though a user who wishes to watch DVD pushes the playback button because it is set to HDD mode. At that time, the disappointment signal is detected by the biological signal processor 100 and the appliance 1A is switched automatically from the HDD mode to the DVD mode in accordance with the instruction of the function switch section 201, thereby playing back the content in DVD mode. Then, the steps b3 and b4 are executed. When the disappointment signal is not detected, the switched function, that is, the DVD mode is maintained and the routine returns to the step b1 for waiting next user's manipulation input.

As described above, in the present embodiment, when the appliance's operation in accordance with the user's manipulation does not match the user's expectation in an appliance having a plurality of different functions, the currently executed function is changed to another function. This eliminates compulsion of annoying manipulation for function selection on the user, enabling smooth appliance manipulation.

For example, in manipulation for recording in a multi function peripheral of VHS and HDD, when a user who wishes to record to VHS inputs date, channel, time, and the like to a remote control and transfers the data to the appliance, HDD may be programmed unlike the user's intention. In this situation, the user must have required to open the program list and change the recorder from HDD to VHS through GUI conventionally. While in the present embodiment, the function is automatically changed in response to the detection of the disappointment signal.

It is noted that the function change described herein is one example and it is needless to say that various modifications are possible on the basis of the subject matter of the present embodiment that the currently executed function is switched to another candidate function through detection of appliance's operation different from user's intention.

In addition, modification may be advised to a user by presenting the currently executed function visually or audibly upon detection of the disappointment signal.

Embodiment 3

Recently, remote controls for operating home use appliances are developed so as to have multifunction and a single remote control becomes capable of controlling a plurality of appliances. For example, in the case where a single remote control is capable of controlling a TV set and a VHS/HDD recorder, channels of the respective appliances can be changed by a common channel key after an appliance to be manipulated is selected in advance. However, when a user watching TV tries to change the channel through the remote control, the channel may remain unchanged and he/she may think "Why? What's wrong with it?" This is because the appliance selection function of the remote control is set to the VHS/HDD rather than the TV set.

In Embodiment 3 of the present invention, in the case where any of appliances operates selectively through manipulation of, for example, a remote control in an appliance system having a plurality of appliances, a target appliance to be controlled is changed automatically through detection of the disappointment signal when the operating appliance is not one as the user intends.

Figure 7:
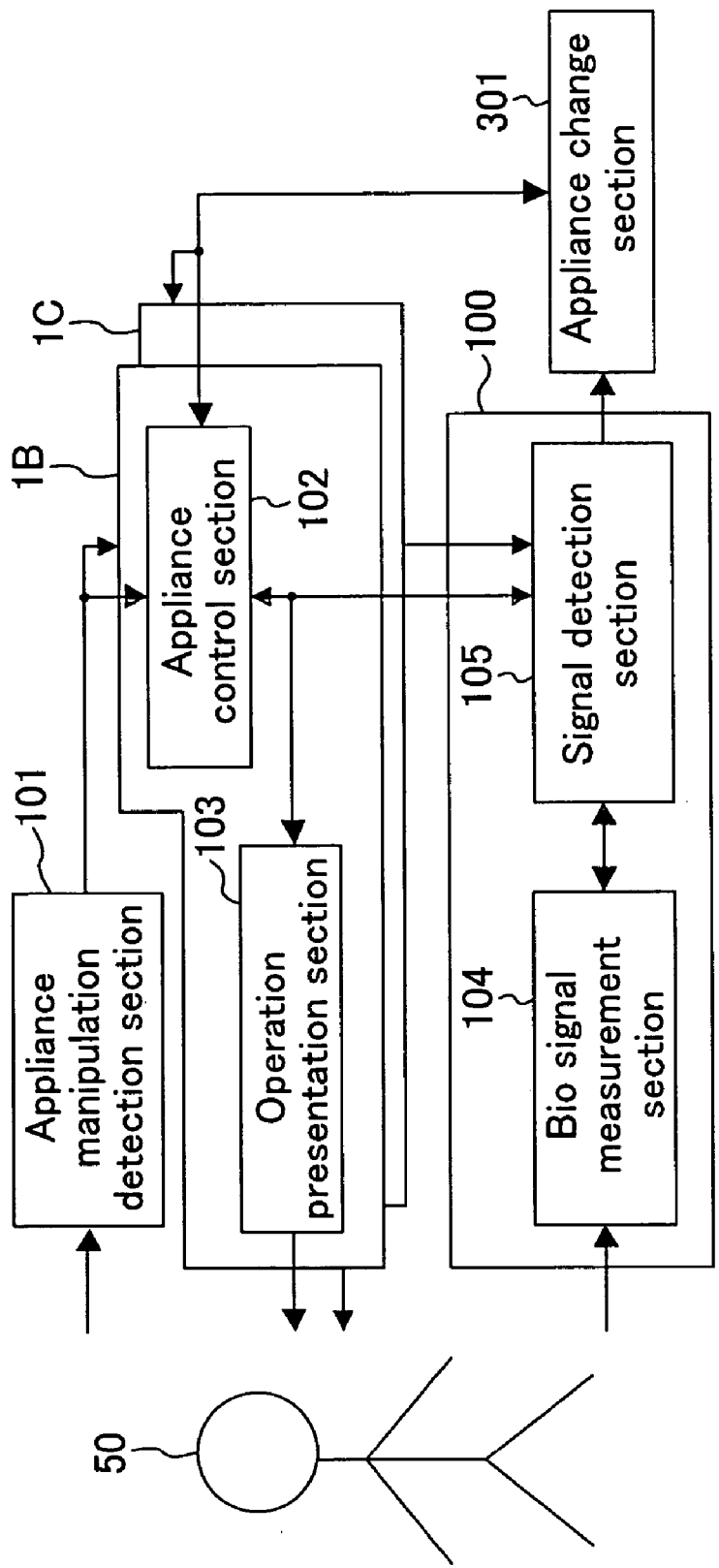
FIG. 7 is a block diagram showing a constitution of a biological signal utilizing appliance system according to Embodiment 3.

FIG. 7 is a block diagram showing a constitution of a biological signal utilizing appliance system according to the present embodiment. In FIG. 7, the same reference numerals as in FIG. 1 and FIG. 5 are assigned to the constitutional element common to those in FIG. 1 and FIG. 5. The constitution in FIG. 7 is provided with a plurality of appliances 1B, 1C each including the appliance control section 102 and the operation presentation section 103, and the biological signal processor 100 is provided separately from the appliances 1B, 1C. An appliance change section 301 instructs the appliance control section 102 to change a target appliance to be controlled when the disappointment signal is detected by the signal detection section 105. The appliance change section 301 may be provided in either of the appliances 1B, 1C or in, for example, the biological signal processor 100 separately from the appliances 1B, 1C.

Figure 8:
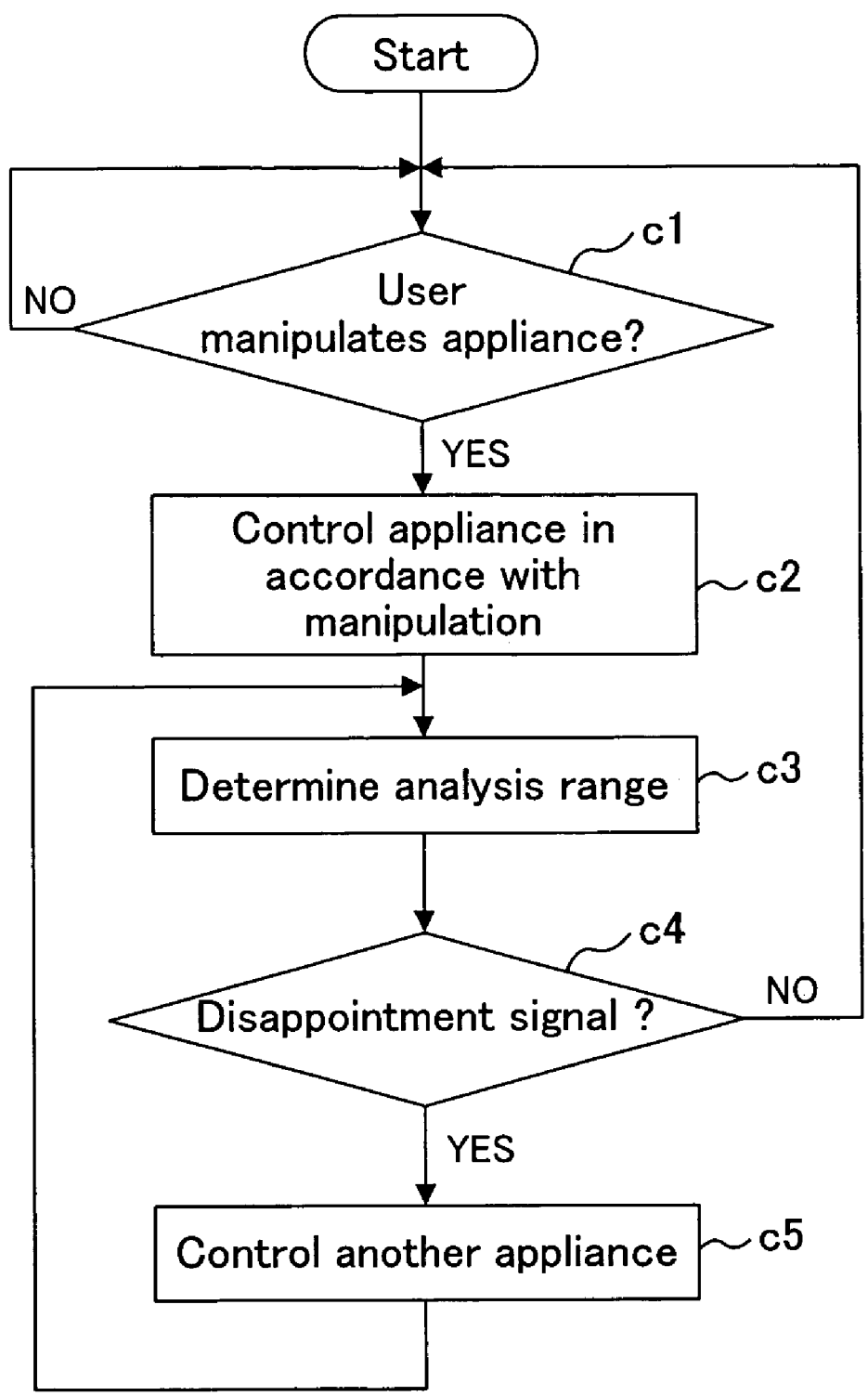
FIG. 8 is a flowchart showing operation of the constitution in FIG. 7.

Operation of the biological signal utilizing appliance system according to the present embodiment will be described with reference to the flowchart of FIG. 8. Wherein, steps c1 to c4 in FIG. 8 are basically the same as the steps a1 to a4 in Embodiment 1 and the detailed description thereof is omitted herein. It is supposed that the appliance 1B is a TV set, the appliance 1C is a VHS/HDD recorder, and they are manipulated through a single remote control including the appliance manipulation detection section 101. Also, each appliance control section 102 of the appliances 1B, 1C has a table for converting a manipulation signal of the other appliance to a control signal of own.

Suppose that the user 50 who wants to change the channel of the TV set 1B pushes a channel key of the remote control in the condition that the appliance selection mode of the remote control is set to the VHS/HDD recorder 1C. At that time, a manipulation signal that the remote control to be send is sent to both the TV set 1B and the VHS/HDD recorder 1C. However, the TV set 1B judges that the signal is not a manipulation signal of own not to change own operation. On the other hand, the VHS/HDD recorder 1C recognizes it as a signal for changing own channel to change own channel.

Though the user 50 expects the channel of the TV set 1B to be changed, only the channel of the VHS/HDD recorder 1C is changed in actual fact and the state of the TV set 1B does not change. Therefore, the disappointment signal is detected (YES in c4).

Accordingly, the target appliance to be controlled is changed in a step c5. In this example, the appliance control section 102 of the TV set 1B references the table and recognizes that the manipulation signal of the VHS/HDD recorder 1C, which has been sent from the remote control previously, is a signal for channel change to change the channel of the TV 1B. Further, the appliance control section 102 of the VHS/HDD recorder 1C cancels the channel change. Then, the steps c3 and c4 are executed. When the disappointment signal is not detected, the routine returns to the step c1 while the state in which the target appliance to be controlled is changed to the TV set 1B is maintained and next user's manipulation input is waited.

As described above, in the present embodiment, when an appliance operating in accordance with user's manipulation through a remote control or the like is different from user's expectation in an appliance system including a plurality of appliances, the control target is changed to another appliance. This eliminates compulsion of annoying manipulation for appliance selection on the user, enabling smooth appliance manipulation.

It is noted that the appliance change described herein is one of examples and it is needless to say that various modifications are possible on the basis of the subject matter of the present embodiment that a target appliance to be controlled is changed through detection of the fact that the appliance operates differently from user's intention.

In addition, appliance change may be advised to a user by presenting the currently selected appliance visually or audibly upon detection of the disappointment signal.

What is claimed is:

1. An appliance that operates utilizing a biological signal, comprising:
   an appliance manipulation detection section that detects appliance's manipulation by a user;
   an appliance control section that controls the appliance in accordance with the manipulation;
   an operation presentation section that presents to the user an operation content of the appliance as a result of the control;
   a biological signal measurement section that measures an electroencephalogram of the user; and
   a signal detection section that detects the presence or absence of an event-related potential in a time range having a starting point in the electroencephalogram of the user, the time range is centered around 750 ms and the starting point being time when the operation content is presented, wherein the signal detection section is embodied as computer executable instructions executed by a processor.

2. The appliance of claim 1, further comprising:
an operation modification section that instructs the appliance control section to cancel the manipulation of the appliance or to change a function that the appliance currently executes to another function.

3. The appliance of claim 2,
wherein the function is performance selected from a group consisting of display, selection, recording, playback, edition, distribution, and deletion of a content composed of at least one of a still image, a moving picture, a video, and audio.

4. An appliance system including the biological signal utilizing appliance of claim 1, comprising:
an appliance change section that instructs the appliance control section to allow another appliance to operate in exchange for an appliance operating in accordance with the manipulation when the event-related potential is detected.

5. The appliance system of claim 4,
wherein the appliance has at least one of functions of display, selection, recording, playback, edition, distribution, and deletion of a content composed of at least one of a still image, a moving picture, a video, and audio.

6. A biological signal processor comprising:
a biological signal measurement section that measures an electroencephalogram of a user; and
a signal detection section that detects the presence or absence of an event-related potential in a time range having a starting point in the electroencephalogram of the user, the starting point being time when the operation content is presented and the time range is centered around 750 ms which is obtained by adding a predetermined shift time of 150 ms to 600 ms.

7. A method for controlling an appliance that utilizes a biological signal, comprising the steps of:
detecting appliance's manipulation by a user;
controlling the appliance in accordance with the manipulation;
presenting to the user an operation content of the appliance as a result of the control;
measuring an electroencephalogram of the user; and
detecting the presence or absence of an event-related potential in a time range having a starting point in the electroencephalogram of the user, the starting point being time when the operation content is presented and the time range is centered around 750 ms which is obtained by adding a predetermined shift time of 150 ms to 600 ms, wherein the detection step is performed by a processor.

8. An appliance that operates utilizing a biological signal, comprising:
an appliance manipulation detection section that detects appliance's manipulation by a user;
an appliance control section that controls the appliance in accordance with the manipulation;
an operation presentation section that presents to the user an operation content of the appliance as a result of the control;
a biological signal measurement section that measures an electroencephalogram of the user; and
a signal detection section that detects the presence or absence of the event-related potential after a time range at a starting point in the electroencephalogram of the user, the starting point being time when the operation content is presented,
wherein the time range is centered around a value obtained by adding a latency shift time to 600 ms, the latency shift time being according to at least one of cognitive complication of the operation content and the user's characteristics.

9. The appliance of claim 8, further comprising:
a latency shift time storage section that stores the latency shift time according to cognitive complication of the operation content and the user's characteristics.

* * * * *